(12) United States Patent
Singh et al.

(10) Patent No.: US 10,973,782 B2
(45) Date of Patent: Apr. 13, 2021

(54) PHARMACEUTICAL COMPOSITION FOR IMPROVING OR PREVENTING PROGRESSION OF CHRONIC KIDNEY DISEASE

(71) Applicant: Frimline Private Limited, Gujarat (IN)

(72) Inventors: Ankit Shyam Singh, Gujarat (IN); Vedprakash Mishra, Gujarat (IN); Neelima Tongra, Rajasthan (IN)

(73) Assignee: Frimline Private Limited, Gujarat (IN)

( * ) Notice: Subject to any disclaimer, the term of this patent is extended or adjusted under 35 U.S.C. 154(b) by 0 days.

(21) Appl. No.: 16/108,947

(22) Filed: Aug. 22, 2018

(65) Prior Publication Data

US 2019/0070133 A1    Mar. 7, 2019

(30) Foreign Application Priority Data

Sep. 5, 2017  (IN) .............................. 201721031443

(51) Int. Cl.
| | | |
|---|---|---|
| *A61K 31/16* | (2006.01) | |
| *A61K 45/06* | (2006.01) | |
| *A61K 31/593* | (2006.01) | |
| *A61P 13/12* | (2006.01) | |
| *A61K 31/353* | (2006.01) | |
| *A61K 31/164* | (2006.01) | |
| *A61K 31/235* | (2006.01) | |
| *A61K 31/7048* | (2006.01) | |
| *A61K 31/352* | (2006.01) | |
| *A61K 9/20* | (2006.01) | |
| *A61K 31/095* | (2006.01) | |
| *A61K 31/355* | (2006.01) | |
| *A61K 31/451* | (2006.01) | |

(52) U.S. Cl.
CPC ................ *A61K 31/16* (2013.01); *A61K 9/20* (2013.01); *A61K 31/164* (2013.01); *A61K 31/235* (2013.01); *A61K 31/352* (2013.01); *A61K 31/353* (2013.01); *A61K 31/593* (2013.01); *A61K 31/7048* (2013.01); *A61K 45/06* (2013.01); *A61P 13/12* (2018.01); *A61K 31/095* (2013.01); *A61K 31/355* (2013.01); *A61K 31/451* (2013.01); *A61K 2300/00* (2013.01)

(58) Field of Classification Search
CPC .............. A61K 2300/00; A61K 31/164; A61K 31/352; A61K 31/16; A61K 31/353; A61K 31/235; A61K 31/593; A61K 31/7048; A61K 45/06; A61K 31/095; A61K 31/355; A61K 31/451; A61K 9/20; A61P 13/12
See application file for complete search history.

(56) References Cited

U.S. PATENT DOCUMENTS

| | | | |
|---|---|---|---|
| 5,506,224 A | 4/1996 | Della Valle | |
| 5,990,170 A | 11/1999 | Della Valle | |
| 8,663,701 B2 | 3/2014 | Della Valle | |
| 2007/0207225 A1* | 9/2007 | Squadrito | A61K 31/353 424/757 |
| 2010/0010005 A1* | 1/2010 | Lines | A61K 31/352 514/252.16 |
| 2013/0085121 A1* | 4/2013 | Wang | A61K 9/2027 514/167 |
| 2015/0065576 A1* | 3/2015 | Della Valle | A61K 31/198 514/616 |
| 2015/0265568 A1* | 9/2015 | Della Valle | A61K 31/164 424/489 |

FOREIGN PATENT DOCUMENTS

| | | |
|---|---|---|
| EP | 1844784 A1 | 10/2007 |
| EP | 2944309 A1 | 11/2015 |
| NL | 2011448 | 1/2015 |
| WO | 1999/60987 A2 | 12/1999 |
| WO | 2001/24645 A1 | 4/2001 |
| WO | 2002/080860 A2 | 10/2002 |
| WO | 2005/046580 A2 | 5/2005 |
| WO | 2011/027373 A1 | 3/2011 |
| WO | 2012/015704 A2 | 2/2012 |
| WO | 2013/028570 A2 | 2/2013 |
| WO | 2013/121449 A1 | 8/2013 |
| WO | 2014/017936 A2 | 1/2014 |
| WO | 2015/007613 A1 | 1/2015 |
| WO | 2015/007615 A1 | 1/2015 |
| WO | 2015/012708 A1 | 1/2015 |
| WO | 2015/016728 A1 | 2/2015 |
| WO | 2015/157313 A1 | 10/2015 |
| WO | 2016/063217 A1 | 4/2016 |

(Continued)

OTHER PUBLICATIONS

Ming Chang Hu et al.; "Klotho deficiency causes vascular calcification in chronic kidney disease"; J. Am Soc. Nephrol; vol. 22; 2011; pp. 124-136.
Tetsu Akimoto et al.; "The relationship between the soluble Klotho protein and the residual renal function among peritoneal dialysis patients"; Clin. Exp. Nephrol; No. 16; 2012; pp. 442-447.
Yoshiko Shimamura et al.; "Serum levels of soluble secreted alpha-Kiotho are decreased in the early stages of chronic kidney disease, making it a probable novel biomarker for early diagnosis"; Clin. Exp. Nephrol; No. 16; 2012; pp. 722-729.

(Continued)

*Primary Examiner* — Michael B. Pallay
(74) *Attorney, Agent, or Firm* — Baker & Hostetler LLP

(57) ABSTRACT

The present application relates to a pharmaceutical composition/formulation for improving or preventing progression of chronic kidney disease (CKD) caused due to inflammation and/or Klotho under expression. More particularly, the invention relates to a composition/formulation comprising a synergistic combination of Palmitoylethanolamide (PEA), Cholecalciferol and one or more natural ingredients. The invention also provides various formulations and methods of preparing the same.

17 Claims, 2 Drawing Sheets

(56) References Cited

FOREIGN PATENT DOCUMENTS

| WO | 2016/146453 A1 | 9/2016 |
|---|---|---|
| WO | 2016/183134 A1 | 11/2016 |
| WO | 2016/185468 A1 | 11/2016 |
| WO | 2016/193905 A1 | 12/2016 |

OTHER PUBLICATIONS

Hirotaka Komaba et al.; "Effects of cinacalcet treatment on serum soluble Klotho levels in haemodialysis patients with secondary hyperparathyroidism"; Nephrol Dial Transplant; No. 27; 2012; pp. 1967-1969.

Mehmet Baha Aytac et al.; "Effect of cholecalciferol on local arterial stiffness and endothelial dysfunction in children with chronic kidney disease"; Pediatr Nephrol; 2015; pp. 1-11.

Yusuf Karakas et al.; "Effect of vitamin D supplementation on endothelial dysfunction in hemodialysis patients: Endothelial dysfunction in hemodialysis patients"; Hemodialysis International; 2016; pp. 1-10.

James B. Wetmore et al; "Cholecalciferol v. ergocalciferol for 25-hydroxyvitamin D (25(OH)D) repletion in chronic kidney disease: a randomised clinical trial"; British Journal of Nutrition; No. 116; 2017; pp. 2074-2081.

Giampiero Colombano et al.; "O-(Triazolyl) methyl carbamates as a novel and potent class of fatty acid amide hydrolase (FAAH) inhibitors"; ChemMedChem; pp. 1-17.

Katerina Otrubova et al.; "The discovery and development of inhibitors of fatty acid amide hydrolase (FAAH)"; Bioorganic & Medicinal Chemistry Letters; No. 21; 2011; pp. 4674-4685.

Michael Eddleston et al.; "Implications of the BIA-102474-101 study for review of first-into-human clinical trials"; British Journal of Clinical Pharmacology; No. 81; 2016; pp. 582-586.

Christophe Mallet et al.; "FAAH inhibitors in the limelight, but regrettably"; International Journal of Clinical Pharmacology and Therapeutics; vol. 54; No. Jul. 2016; pp. 498-501.

Rimplejeet Kaur et al.; "What failed BIA 10-2474 Phase I clinical trial? Global speculations and recommendations for future Phase I trials"; Journal of Pharmacology and Pharmacotherapeutics; vol. 7; Issue 3; Jul.-Sep. 2016; pp. 120-126.

* cited by examiner

PHARMACEUTICAL COMPOSITION FOR IMPROVING OR PREVENTING PROGRESSION OF CHRONIC KIDNEY DISEASE

FIELD OF THE INVENTION

The present invention relates to a pharmaceutical composition/formulation for improving or preventing progression of chronic kidney disease (CKD) caused by inflammation and/or Klotho under expression. More particularly, the invention relates to a pharmaceutical composition/formulation comprising a synergistic combination of Palmitoylethanolamide (PEA), Cholecalciferol and one or more natural ingredients. The invention also provides various formulations and methods of preparing the same.

BACKGROUND OF THE INVENTION

Kidney diseases continue throughout the patient's life and when progress at a certain frequency, sometimes ultimately leads to terminal renal failure.

In kidney/renal failure there is a decrease in the glomerular filtration rate and the kidneys are unable to maintain homeostasis of the blood. Homeostatic balance of water, sodium, potassium, calcium and other salts is no longer possible and nitrogenous wastes are not excreted. Retention of water causes edema and as the concentration of hydrogen ions increases, acidosis develops. Nitrogenous wastes accumulate and a condition referred to as uremia develops in the blood and tissue. Uremic toxins can be defined as solutes that:

(i) are normally excreted by healthy kidneys;
(ii) accumulate progressively during the development of renal failure so that their concentration increases, and
(iii) inhibit various physiologic and biochemical functions.

As a whole, these contribute to a complex set of clinical symptoms that comprise the Uremic Syndrome. Examples of uremic toxins include, but are not limited to, ammonia, urea, creatinine, phenols, indoles, and middle molecular weight molecules. More specifically, in uremia, the concentration of serum creatinine, blood urea nitrogen (BUN), uric acid, and guanidino compounds such as N-methyl guanidine and guanidino succinic acid are significantly altered with accompanying abnormalities in acid-base equilibrium, electrolytes and water retention.

In addition, there are several known and unknown substances of low and middle molecular weight which have been identified as uremic toxins which also accumulate. Further, as a result of poor clearance of waste products of metabolism, there are compensatory and adaptive processes which complicate the condition. If untreated, the acidosis and uremia can cause a coma and eventually result in death.

Creatinine serves as an important marker for kidney function. Creatinine is a non-proteinous nitrogen compound produced within the muscles and is as an excellent indicator of renal function (glomerular filtration rate) that is not influenced by extrinsic factors such as the diet. As the kidney disease progresses and renal function falls below 50% of the normal level, the serum creatinine begins to rise. At this stage, the primary approach is dietary therapy where protein and salt intake is restricted, with adjuvant pharmacotherapy. However, when renal function drops to a level of 20 to 30% or less, renal failure arises, at which point serum creatinine levels will not normalize with a dietary therapy. At a renal function of 5 to 10% or below, renal dialysis is necessary.

A progression degree of the chronic renal failure is generally classified from stage 1 to stage 5 according to a classification of chronic kidney disease (CKD) (Clinical Practice Guidebook for Diagnosis and Treatment of Chronic Kidney Disease 2012, The Japanese Journal of Nephrology 2012). The incidence of CKD is increasing in both developed and developing nations. It is estimated that CKD affect 17% of adult population worldwide.

CKD is diagnosed by a urine protein and a glomerular filtration rate (GFR), ml/min/1.73 $m^2$) in routine clinical practice and evaluated with estimated GFR (eGFR) calculated with the blood concentration of creatinine (Cr) based on age and gender using Japanese equation for estimating GFR in a routine diagnosis. The GFR is an index for measuring the renal function (capacity of the kidney to excrete body wastes into urine) and the value becomes lower with reduction in the renal function.

In stage 1 of CKD, the GFR value is in the normal range (GFR>=90) although kidney damage is present.

In stage 2, kidney damage is present with the GFR value slightly lower than normal (60 to 89). In these stages, there is still remaining renal function with almost no symptoms.

In stage 3 of CKD, kidney damage is present with the medium GFR value (30 to 59). In this stage, the size of remaining renal function becomes incomplete, thereby causing an increase in the amount of urine and the blood concentration of urea nitrogen, and mild anemia. As a result, it becomes difficult to maintain homeostasis of the body fluid.

In stage 4 of CKD, kidney damage is present with the GFR value (15 to 29). In this stage, the symptoms in stage 3 are exacerbated. It is noted that CKD in stages 1 to 4 is called conservative stage renal failure, representing a condition prior to starting the dialysis therapy.

Finally, in stage 5 of CKD, end stage renal failure is developed and the dialysis therapy becomes necessary (GFR<15). In this stage, uremic symptoms become apparent with the progression of abnormality in the body fluid.

The role of inflammation in the progression of CKD is evident in the glomerulopathies diseases in which inflammation has been classically recognized, as well as in congenital malformations of the kidneys and urinary tract, conditions in which mechanical obstruction was traditionally thought to be the principal mechanism. The potential of some cytokines and chemokines as biomarkers of CKD progression, such as transforming growth factor beta (TGF-β), a protein which is chemotactic for type 1 monocytes (MCP-1/CCL2) and interleukin-8 (IL-8/CXCL8), is also emphasized. Inflammation is a cause of CKD progression, and CKD is characterized by a progressive loss of renal function, chronic inflammation, oxidative stress, vascular remodeling, and glomerular and tubule-interstitial scarring.

The Klotho gene encodes a single-pass transmembrane protein and is expressed primarily in the kidney. The Klotho protein is composed of a large extracellular domain, a transmembrane domain, and a very short intracellular domain (10 amino acids). Klotho protein exists in two forms: membrane Klotho and secreted Klotho. Membrane Klotho functions as a receptor for a hormone that regulates excretion of phosphate and synthesis of active vitamin D in the kidney. Secreted Klotho functions as a humoral factor with pleiotropic activities, including suppression of growth factor signaling, suppression of oxidative stress, and regulation of ion channels and transporters.

In CKD, Klotho deficiency exerts a significant impact on progression of renal disease and extra renal complications. Klotho levels may be an indicator of early disease and predict the rate of progression, and presence and severity of soft tissue calcification in CKD. The correction of Klotho deficiency may delay progression and forestall development of extra renal complications in CKD. Urinary Klotho levels of CKD patients were shown to significantly decrease at a very early stage and were sustainably reduced with the progression of CKD [Hu M C et al Klotho deficiency causes vascular calcification in chronic kidney disease. *J Am Soc Nephrol* 2011; 22: 124-136; Akimoto T et al. The relationship between the soluble Klotho protein and the residual renal function among peritoneal dialysis patients [*Clin Exp Nephrol* 2012]. Moreover, Klotho levels in the plasma, urine and kidney were decreased in parallel in the CKD rodent model. Animal studies have shown the decline in Klotho levels in the plasma, urine and kidneys with a decrease in creatinine clearance also in CKD [Hu M C, Zhang J et al. Klotho deficiency causes vascular calcification in chronic kidney disease. *J Am Soc Nephrol* 2011; 22: 124-136].

Similarly, human urinary Klotho excretion is significantly decreased and the amount of urinary Klotho is correlated with eGFR [Akimoto T, Shiizaki K, Sugase T et al. The relationship between the soluble Klotho protein and the residual renal function among peritoneal dialysis patient [*Clin Exp Nephrol* 2012]. Moreover, reduced soluble Klotho in plasma is correlated with a decline in eGFR in both CKD patients [Shimamura Y, Hamada K, Inoue K et al. Serum levels of soluble secreted alpha-Klotho are decreased in the early stages of chronic kidney disease, making it a probable novel biomarker for early diagnosis [*Clin Exp Nephrol* 2012] and ESRD patients on hemodialysis [Komaba H, Koizumi M, Tanaka H et al. Effects of cinacalcet treatment on serum soluble Klotho levels in haemodialysis patients with secondary hyperparathyroidism *Nephrol Dial Transplant* 2011].

Examples of major causative diseases of chronic renal failure include diabetic nephropathy, chronic nephritis (chronic glomerulonephritis), nephrosclerosis, and the like.

Development of end stage renal failure causes an exceedingly high mortality risk without performing the dialysis therapy that alternates the renal function or a kidney transplant. In general, a recommended criterion for initiation of the dialysis therapy is a blood concentration of creatinine of 8 mg/dl or more or a blood concentration of urea nitrogen of 100 mg/dl or more.

Dialysis therapy is a therapeutic method for artificially purifying the blood by dialysis when body wastes cannot be removed due to renal failure and uremia. The introduction of renal dialysis has contributed to rapid progress in the clinical treatment of renal failure and elucidation of uremia. Dialysis can serve as a lifetime therapy for End-Stage Renal Disease (ESRD) patients. Phosphate binders such as calcium acetate, calcium carbonate or aluminum hydroxide are generally prescribed for uremic patients receiving dialysis to reduce elevated phosphate levels. In general, however, dialysis is very expensive, inconvenient, time consuming and may occasionally produce one or more side effects. With a successful kidney transplant, a patient can live a more normal life with less long-term expense. However, there are also high costs associated with transplant surgery, the recovery period and the continuous need for anti-rejection medications. Further, there are often times a shortage of suitable donors. Accordingly, there is a need for alternative strategies and easily available options.

CKD is a major health problem in today's society having currently no cure. The goals of existing therapy are to slow the progression of disease; treat underlying causes and contributing factors; treat complications of disease; and replace lost kidney function. Current standard of care for CKD is aimed at renoprotective effects, such as proteinuria reduction and decreased rate of GFR decline, by using treatment with angiotensin modulators, particularly the angiotensin-converting enzyme (ACE) inhibitors and the angiotensin II receptor blockers (ARBs). These are antihypertensive agents that also have the effect of reducing albuminuria and slowing the decline of renal function. However, despite treatment with these drugs, many CKD patients continue to experience loss in renal function at a rate that is significantly faster than normal age-related decline. No new disease modifying treatments for CKD have been approved by the FDA in the last decade. Accordingly, there exists an urgent need for drugs or nutraceutical supplements for improving or preventing progression of CKD exhibiting no side effects in pharmacotherapy and is easy to ingest for a long time.

Palmitoylethanolamide (PEA) is an endogenous fatty acid amide belonging to the family of the N-acylethanolamines. Several studies have demonstrated that PEA is an important analgesic, anti-inflammatory, and neuroprotective mediator, acting at several molecular targets in both central and sensory nervous systems as well as immune cells. Some clinical studies have demonstrated that PEA reduces the renal dysfunction and injury associated with ischemia reperfusion of the mouse kidney and reduces mast cell infiltration and activation, which occurs not only in inflammation, but also in inflammatory hyperalgesia and neuropathic hyperalgesia. Hence, because of its important pharmacological properties and a good safety profile, PEA could represent an alternative approach to delay renal disease progression including progression of CKD.

Vitamin D is available in two different forms, ergocalciferol (vitamin D2) and cholecalciferol (vitamin D3). These are officially regarded as equivalent and interchangeable. Cholecalciferol is the form of vitamin D that is naturally made by human bodies after the skin is exposed to direct sunlight. It can also be found in vitamin supplements and foods, such as fortified milk, fatty fish, fish liver oil and egg yolks. However, the body can't use cholecalciferol until it is changed into an active form of vitamin D by the liver and kidneys. Cholecalciferol is naturally found in the human body and generally considered the preferred form of vitamin D supplementation. Aytac et al. reported a favorable effect of high-dose cholecalciferol on cardiovascular and endothelial parameters of children with CKD by using flow-mediated dilatation, arterial stiffness, homocysteine, and von Willebrand factor measurements. Karakas et al. confirmed that eight weeks of Cholecalciferol improved the percentage of flow-mediated dilatation in dialysis with CKD patients. Wetmore et al. reported that therapy with cholecalciferol, compared with ergocalciferol, is more effective at raising serum 25(OH)D level in non-dialysis-dependent CKD patients using the same dosage (50,000 IU weekly).

Cannabinoid-based medicines have therapeutic potential for the treatment of pain. Augmentation of levels of endocannabinoids with inhibitors of fatty acid amide hydrolase (FAAH) is analgesic. FAAH is a membrane-bound serine hydrolase that belongs to the amidase signature family of hydrolases. FAAH enzyme breaks down fatty acid amides such as anandamide (N-arachidonoylethanolamide), N-oleoylethanolamide (N-OEA), PEA and oleamide. FAAH belongs to a large and diverse class of enzymes referred to as the amidase signature (AS) family. FAAH Inhibitors are a class of molecules that inactivate the FAAH Enzymes by preventing the hydrolysis of anandamide, oleoylethanolamide and PEA and thereby increasing their endogenous levels. Known chemically synthesized FAAH inhibitors are BIA 10-2474, URB524, URB597, URB694URB937, etc. These inhibitors are disclosed in the article titled "O-(Triazolyl) methyl carbamates as a novel and potent class of fatty acid amide hydrolase (FAAH) inhibitors" published by Colombano et al and the article titled "The discovery and development of inhibitors of fatty acid amide hydrolase (FAAH) published by Otrubova et al.

RELATED PRIOR ARTS

U.S. Pat. No. 5,990,170 discloses a method of synthesis of PEA.

U.S. Pat. No. 5,506,224 refers to a method for treating diseases involving mast cell degranulation, as a consequence of a neurogenic and/or immunogenic hyper-stimulation, comprising the administration of an effective amount of a series of compounds included in a general formula, comprising also the PEA.

EPI082292 discloses a composition comprising anandamide and PEA for activating CB1 and CB2 like cannabinoid receptors for treatment of pain.

WO2001/024645 discloses a nutritional or therapeutic composition for oral administration, which comprises a naturally occurring precursor that is metabolized to a compound having anandamide activity for use as a medicament, in which such precursor is a long chain polyunsaturated fatty acid (LCPUFA) (e.g. arachidonic acid ARA or docosahexaenoic acid DHA) or a derivative thereof having a given general formula. According to an embodiment reported in such application, the composition also comprises an inhibitor of an anandamide inactivating enzyme (amidase), which is said to include PEA. However, no biological effects or further technical results of such hypothetical combination comprising PEA have been shown in such document.

WO2002/080860 and WO2005/046580 refers to a method of reducing food intake or reducing appetite in a mammal, said method comprising orally administering a fatty acid alkanolamide compound, derivative, homolog, or analog. PEA is reported to be one of such fatty acid alkanolamide compounds.

WO2011/027373 A1 discloses a pharmaceutical composition containing an ultra-micronized form of PEA, in which more than 90% by weight of PEA has particle sizes lower than 6 microns (mm).

NL2011448 discloses a pharmaceutical composition comprising PEA particles and/or pharmaceutically acceptable esters or salts thereof, in which the PEA particles are substantially free of pharmaceutical excipients.

WO2013/121449 discloses a use of chemically synthesized FAAH/NAAH inhibitor in association with oxazoline of PEA, for a combined, separate or sequential administration.

U.S. Pat. No. 8,663,701 relates to a pharmaceutical composition for human or veterinary use, containing a therapeutically efficient amount of PEA in the ultra-micronized form, wherein more than 90% by weight of PEA has particle sizes lower than 6 microns, together with pharmaceutically acceptable excipients.

EP1844784 relates to a pharmaceutical composition comprising amides of mono- and di-carboxylic acids and hydroxystilbenes for the treatment of pathologies caused, sustained and/or characterised by an abnormal general response of the immune system, in both humans and animals. More particularly, the invention relates to a pharmaceutical composition comprising one or more of the N-acylethanolamine derivatives selected from N-palmitoylethanolamine, N-(2-hydroxyethyl)-lauroylamide, N,N'-bis (2-hydroxyethyl)nonandiamide, N,N'-bis(2-hydroxyethyl)-2-dodecendiamide, N,N-bis(2-hydroxyethyl)-lauroylamide and one or more of the hydroxystilbenes selected from resveratrol and the glycosides of resveratrol.

WO2016146453 relates to a composition comprising PEA and a vitamin B. The present invention also relates to such a composition for use as a nutraceutical or use as a medicament, for use as an analgesic pharmaceutical, and more specifically for use as an analgesic pharmaceutical in the alleviation of neuropathic pain, and to a method for preparing such a composition.

EP2944309 and WO2016/185468 disclose a pharmaceutical composition comprising a combination of PEA and Opioid for the treatment of pain.

WO2016/063217 discloses a combination of PEA and Spirulina for the treatment of inflammatory states.

WO2016/183134 provides compositions comprising PEA, and an anti-inflammatory or anti-pain component.

WO2016/193905 discloses a pharmaceutical composition comprising a combination of PEA and lycopene, and/or pharmaceutically acceptable salts and/or derivatives thereof.

There are several patent applications (WO 2012/015704, WO 2013/028570, WO 2014/017936, WO 2015/07613, WO 2015/07615, WO 2015/012708, WO 2015/016728, WO 2015/157313), which disclose chemically synthesized different types of FAAH inhibitors which elevate PEA level. However, these chemically synthesized FAAH inhibitors may have side effects upon administration in humans or animals. Several studies reveal the serious side-effects (including death) of chemically synthesized FAAH inhibitors. Some of them include Eddleston Michael et al; "Implications of the BIA-102474-101 study for review of first-into-human clinical trials", Br J Clin Pharmacol (2016) 81 582-586; Mallet et. al.; "FAAH inhibitors in the limelight, but regrettably", International Journal of Clinical Pharmacology and Therapeutics, Vol. 54—No. 7/2016 (498-501); and Kaur et al." "What failed BIA 10-2474 Phase I clinical trial? Global speculations and recommendations for future Phase I trials", J. Pharmacol Pharmacotherapy, 2016 Jul.-Sep. 7(3):120-126.

Several clinical studies corroborate the importance of inflammation in the pathophysiology of CKD but the mechanisms through which inflammation leads to deterioration of the renal function have not been fully elucidated. A defect in Klotho expression in mice leads to a syndrome resembling aging whereas overexpression of Klotho in mice extends life span. Renal Klotho RNA is markedly decreased in CKD patients with etiologies including obstructive nephropathy, rejected transplanted kidneys, diabetic nephropathy, chronic glomerulonephritis, and unknown causes. However data on plasma Klotho levels in human CKD is limited. Thus, inflammation and under expression of Klotho gene serve as huge factors in further enhancing the degradation of the kidney and aggravating the CKD condition in patients.

With the increasing prevalence of obesity, hypertension and type 2 diabetes; there has also been an increase in the prevalence of CKD. Complications of CKD include progression to end stage renal disease and need for costly dialysis or renal transplantation, bone disease and premature cardiovascular disease (CVD) morbidity and mortality. Strategies to manage CKD are thus a high priority, not only from a clinical, but also a public health perspective.

Currently available documents disclose the use of PEA in combination with chemically synthesized FAAH inhibitors and there can be side effects due to synthetic ingredients. Hence there is a requirement to develop formulations which use natural ingredients, including natural FAAH inhibitors. Further, there is also requirement to provide a highly effective relieve for improving or preventing progression of CKD caused due to inflammation and/or Klotho under expression by PEA and its combination with other active ingredients without any side effects in humans or animals accompanied with good tolerability at an effective dose and good safety profile. Hence, there exists a need for combinations of PEA which are highly effective in improving or preventing progression CKD caused due to inflammation and/or Klotho under expression, accompanied by acceptable safety profile and without any adverse effects.

SUMMARY OF THE INVENTION

The present application provides a composition/formulation for treating patients in all stages of CKD. The invention has beneficial aspects especially for those patients who are diagnosed with higher level of creatinine, blood urea nitrogen (BUN) and Interleukin-6 (IL-6) in serum and having lower glomerular filtration rate (GFR) in urine common in dialysis patients.

The pharmaceutical composition/formulation of the present invention is particularly useful for preventing or delaying the need for dialysis in kidney patients and to reduce the frequency and/or duration of dialysis.

The present application provides a pharmaceutical composition/formulation comprising a synergistic combination of Palmitoylethanolamide (PEA), naturally occurring FAAH Inhibitor(s) and Cholecalciferol.

In an exemplary aspect, the present invention provides a pharmaceutical composition/formulation comprising a synergistic combination of PEA, at least one naturally occurring FAAH inhibitor and Cholecalciferol.

In a preferred aspect, the present invention provides a pharmaceutical composition/formulation for improving or preventing progression of CKD, wherein said composition/formulation comprises a synergistic combination of PEA, at least one naturally occurring FAAH inhibitor, Cholecalciferol and a pharmaceutically acceptable excipient.

In a further preferred aspect, the pharmaceutical composition/formulation of the present invention additionally comprises natural antioxidants, vitamins, coenzymes or a combination thereof.

In another aspect of the present application, a process for the preparation of a composition/formulation is described. The process comprises (a) individually weighing the ingredients and sieving through a suitable sieve, (b) mixing the previously weighed ingredients, (c) preparing a dough by adding a binder solution to the mixed ingredients and sieving to obtain granules, (d) drying the granules till the level of dryness (LOD) is reduced to 1.3 to 1.7% w/w to obtain semi dried granules, and (e) sieving the semi dried granules through a suitable sieve to obtain the composition/formulation. The process further comprises adding lubricants or glidants to the semi dried granules and compressing the granules into tablet.

In a preferred aspect, the application provides a process for preparing the composition/formulation of the present invention. The process comprises sifting previously weighed PEA, Natural FAAH Inhibitor(s), optionally added natural anti-oxidant(s), diluent(s), and disintegrating agent(s) separately through a sieve, mixing the contents to obtain a mixture, preparing a binder solution containing cholecalciferol, adding the binder solution to the mixture obtained above and obtaining granules, drying the obtained granules to obtain semi dried granules and sifting the semi dried granules through a sieve, sifting previously weighed lubricant(s) or glidant(s) separately through a sieve and mixing with the sifted semi dried granules to obtain a blend of the composition/formulation. The blend is further compressed into a tablet.

DETAILED DESCRIPTION OF THE INVENTION

Figure 1:
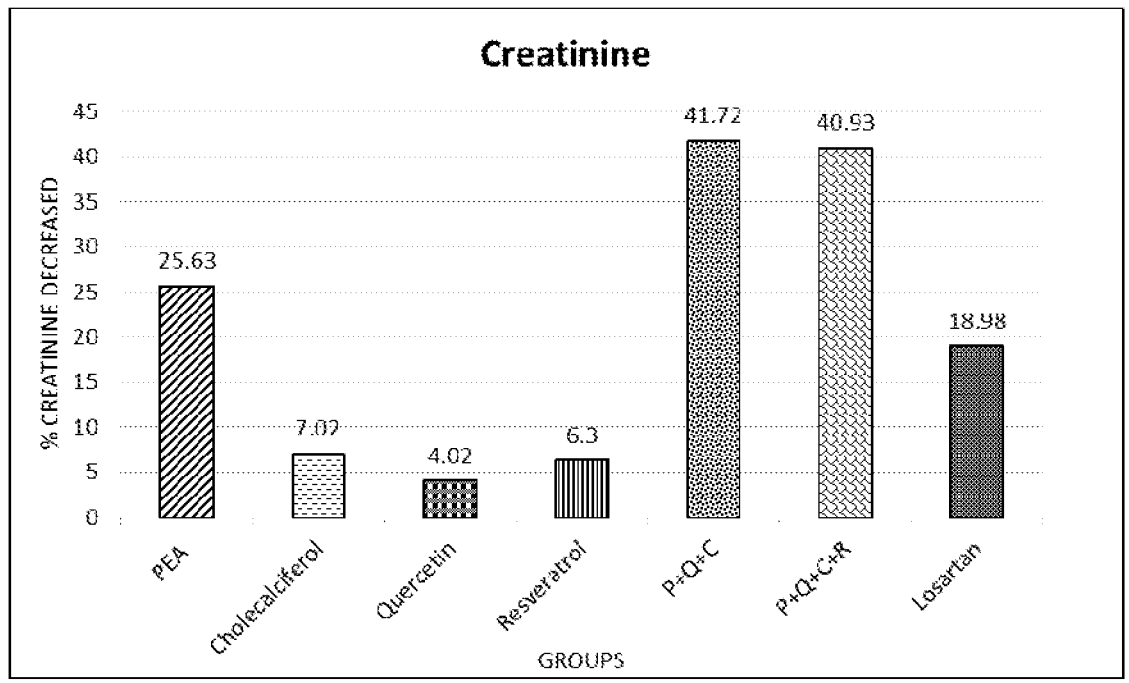
FIG. 1: A comparative study of the serum analysis by percentage decrease in creatinine and effect of administration of test composition/formulation against 5/6 Nephrectomy induced chronic kidney disease in rat.
Figure 2:
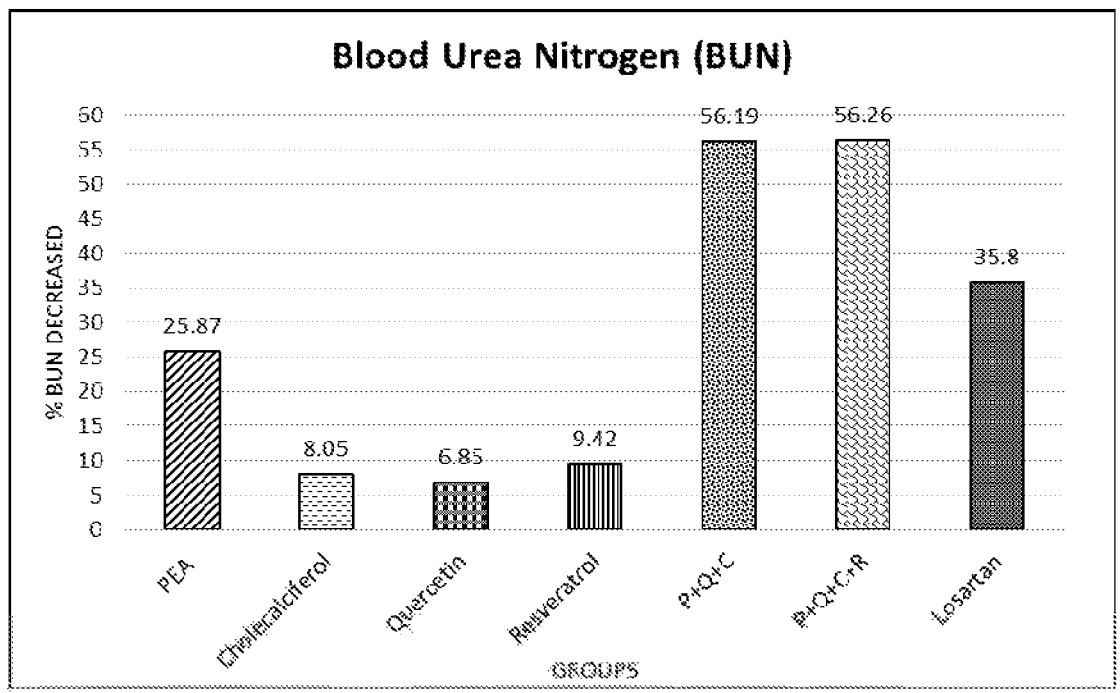
FIG. 2: A comparative study of the serum analysis by percentage decrease in blood urea nitrogen (BUN) and effect of administration of test composition/formulation against 5/6 Nephrectomy induced chronic kidney disease in rat.
Figure 3:
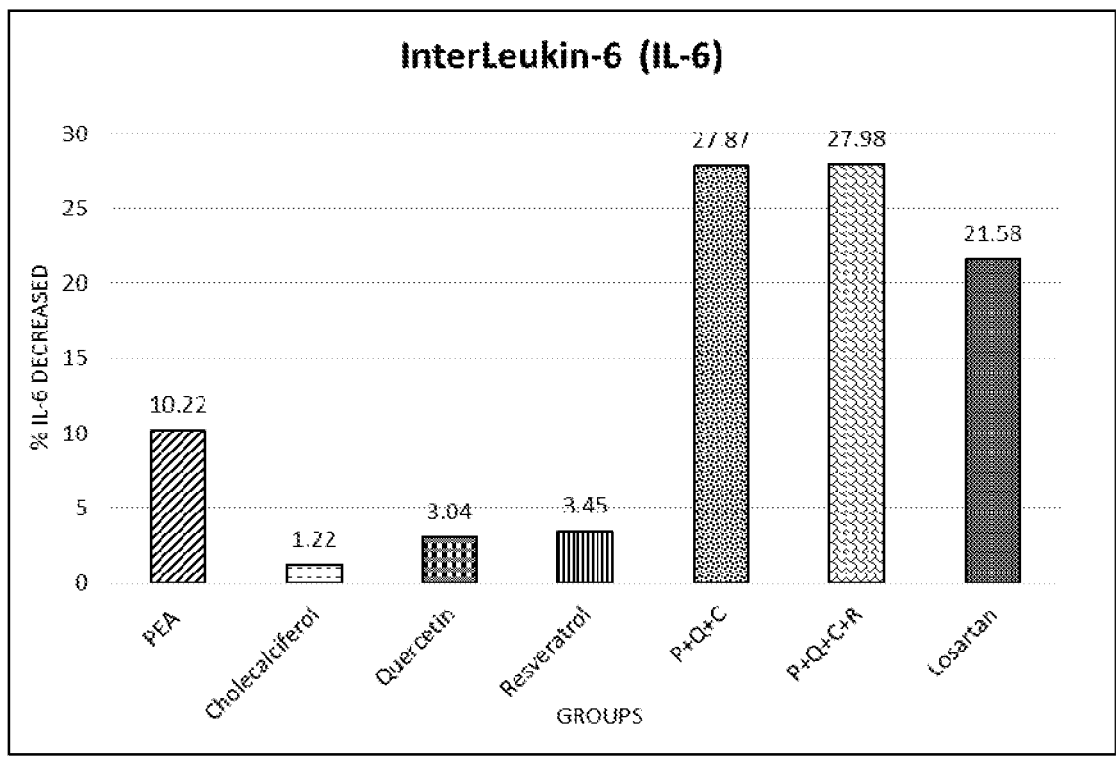
FIG. 3: A comparative study of the serum analysis by percentage decrease in interleukin-6 and effect of administration of test composition/formulation against 5/6 Nephrectomy induced chronic kidney disease in rat.
Figure 4:
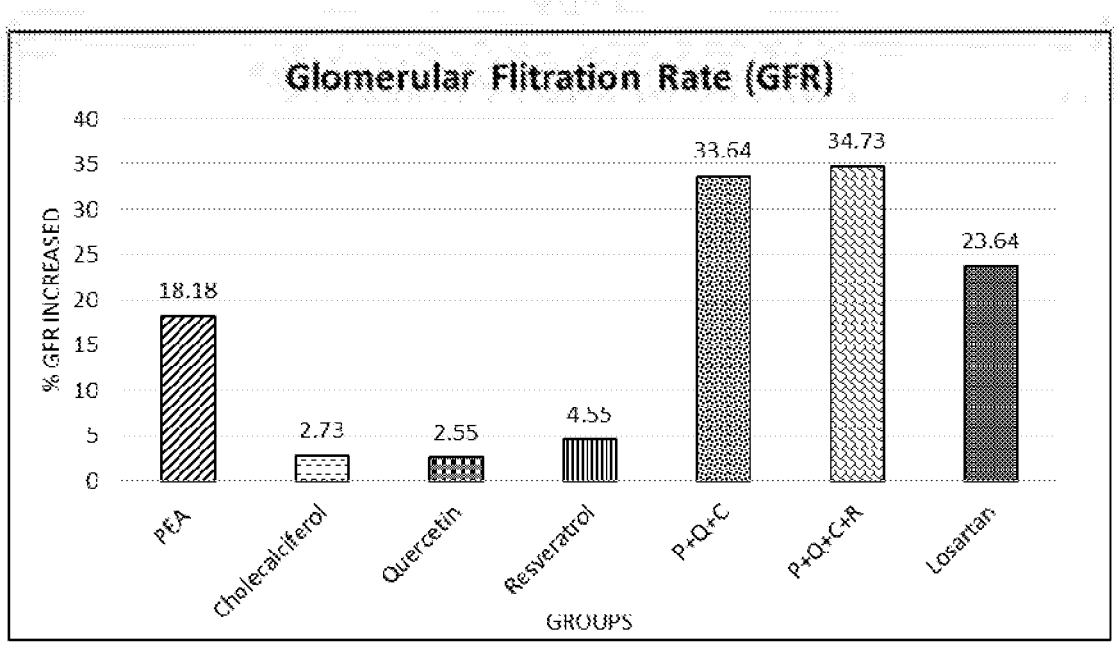
FIG. 4: A comparative study of the urine analysis by percentage increase in glomerular filtration rate and effect of administration of test composition/formulation against 5/6 Nephrectomy induced chronic kidney disease in rat.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected along with the present pharmaceutical carriers. Further, the responses may vary depending upon the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

The present invention is directed to a pharmaceutical composition/formulation comprising a synergistic combination of PEA, cholecalciferol and one or more natural ingredients for improving or preventing progression of chronic kidney disease (CKD). In this regard, the inventors carried out an extensive research studies along with pre-clinical studies and found that the combination of PEA, Cholecalciferol and one or more natural ingredients provides synergistic effect for improving or preventing progression of CKD caused due to inflammation and/or Klotho under expression.

An object of the present invention is to provide a composition/formulation comprising a synergistic combination of PEA with at least one naturally occurring FAAH Inhibitor and cholecalciferol.

In one aspect, the composition/formulation of the present invention may optionally comprise Natural Antioxidant(s).

The PEA composition/formulation of the present invention is able to provide a safe pharmaceutical composition/formulation of PEA with one or more natural ingredients with enhanced and/or synergistic effects compared to PEA alone in the treatment or preventing progression of CKD due to causes of inflammation and/or Klotho under-expression.

Another object of the present invention is to provide a composition/formulation comprising a synergistic combination of PEA along with at least one naturally occurring FAAH Inhibitor and Cholecalciferol to avoid side effects associated with use of synthetic FAAH inhibitor.

In a preferred aspect, the ratio of PEA:Natural FAAH Inhibitors:Cholecalciferol is in a range of 33-92:0.99-62:0.08-7.41. In a more preferred aspect, the ratio of PEA:Natural FAAH Inhibitors:Cholecalciferol is 54:18:0.15.

Another object of the present invention is to provide a synergistic combination of PEA along with at least one naturally occurring FAAH Inhibitor, Cholecalciferol and optionally includes Natural Antioxidants.

The composition/formulation of the present invention comprises natural ingredients including natural FAAH Inhibitor, which not only prevents degradation of PEA from FAAH enzyme in the body, but also exert synergistic effect with PEA and Cholecalciferol or along with other optional ingredients like anti-oxidant in preventing progression of CKD caused due to inflammation and/or Klotho under-expression.

From the available prior art, it is known that PEA and Cholecalciferol play an important role in the disease management of CKD individually. In humans and animals with CKD, the systemic expression of Klotho is decreased, resulting into Klotho deficiency, which may contribute to decline in GFR. Thus, Klotho deficiency plasma is correlated with a decline in eGFR in both CKD patients and ESRD patients on hemodialysis.

The pharmaceutical composition/formulation of the present invention helps to improve the GFR rate in urine by increasing filtration rate. Hence, improvement GFR leads to correction of Klotho deficiency. This may help delay progression and forestall development of extra renal complications in CKD.

The pharmaceutical composition/formulation of the present invention also helps improve kidney function by decreasing creatinine level, BUN level and IL-6 level in serum.

The pharmaceutical composition/formulation of the present invention comprises PEA in micronized or non-micronized form. The amount of PEA in the pharmaceutical composition/formulation of the present invention ranges from 30% by wt. to 70% by wt. of the composition/formulation. In an embodiment, the amount of PEA ranges from 35 to 70% by weight. In another embodiment, the amount of PEA ranges from 40 to 70% by weight. In yet another embodiment, the amount of PEA ranges from 45 to 70% by weight. In yet another embodiment, the amount of PEA ranges from 50 to 70% by weight. In yet another embodiment, amount of PEA ranges from 55 to 70% by weight. In yet another embodiment, the amount of PEA ranges from 60 to 70% by weight. In yet even another embodiment, the amount of PEA ranges from 65 to 70% by weight.

In a preferred embodiment, the pharmaceutical composition/formulation of the present invention comprises PEA in micronized or non-micronized form, wherein the amount of PEA in the pharmaceutical composition/formulation ranges from 150 mg to 2400 mg per unit dose.

The pharmaceutical composition/formulation at the present invention comprises at least one natural FAAH Inhibitors selected from Quercetin, Myricetin, Isorhamnetin, Kaempferol, Pristimerin, Biochanin A, Genistein, Daidzein or the like. The amount of natural FAAH Inhibitor in the pharmaceutical composition/formulation of the present invention ranges from 0.5% by wt. to 60% by wt. of the composition/formulation. In an embodiment, the amount of natural FAAH Inhibitor ranges from about 1 to 60% by weight. In an embodiment, the amount of natural FAAH Inhibitor ranges from about 5 to 60% by weight. In another embodiment, the amount of natural FAAH inhibitor ranges from about 10 to 60% by weight. In an embodiment, the amount of natural FAAH inhibitor ranges from about 20 to 60% by weight. In a further embodiment, the amount of natural FAAH Inhibitor ranges from about 30 to 60% by weight. In yet even another embodiment, the amount of natural FAAH Inhibitor ranges from about 40 to 60% by weight. In yet a further embodiment, the amount of natural FAAH Inhibitor ranges from about 50 to 60% by weight.

In a preferred embodiment, the pharmaceutical composition/formulation of the invention comprises at least one natural FAAH Inhibitors selected from Quercetin, Myricetin, Isorhamnetin, Kaempferol, Pristimerin, Biochanin A, Genistein, Daidzein or the like, wherein the amount of natural FAAH Inhibitor in the pharmaceutical composition/formulation ranges from 2 mg to 3000 mg per unit dose.

The pharmaceutical composition/formulation of the invention comprises Cholecalciferol. The amount of Cholecalciferol in the pharmaceutical composition/formulation of the present invention ranges from 0.05% by wt. to 10% by wt. of the composition formulation.

In a preferred embodiment, the pharmaceutical composition/formulation of the invention comprises Cholecalciferol, wherein the amount of Cholecalciferol in the pharmaceutical composition/formulation ranges from 100 IU to 60,000 IU per unit dose. (Conversion factor 1 IU≅0.002 mg)

The pharmaceutical composition/formulation of the invention optionally comprises at least one Natural Antioxidant. The said Natural Antioxidants are selected from Resveratrol, Vitamin E, glutathione, selenium or the like. The amount of Natural Antioxidant in the pharmaceutical composition formulation of the present invention ranges from 0.04% by wt. to 50% by wt. of the composition formulation.

In a preferred embodiment, the pharmaceutical composition/formulation of the present invention comprises at least one Natural Antioxidant selected from Resveratrol, Vitamin E, glutathione, selenium or the like, wherein the natural Antioxidant in the pharmaceutical composition/formulation ranges from 0.2 mg to 500 mg per unit dose.

In even another aspect, the pharmaceutical composition/formulation of the present invention comprises a synergistic combination of PEA, Quercetin, and Cholecalciferol.

In even another aspect, the pharmaceutical composition formulation of the present invention comprises a synergistic combination of PEA, Quercetin, Cholecalciferol and resveratrol.

The composition/formulation of the present invention optionally comprises vitamins, co-enzymes or combination thereof. The pharmaceutical composition/formulation of the present invention further comprises vitamins selected from methylcobalamin, cyanocobalamin, benfotiamine or the like. The amount of vitamins in the pharmaceutical composition/formulation of the present invention ranges from 0.01% by wt. to 10% by wt. of the composition. The amount of vitamins in the pharmaceutical composition/formulation of the present invention ranges from 0.1 mg to 200 mg per unit dose.

The pharmaceutical composition/formulation of the present invention further comprises co-enzymes selected from ubidecarenone, thiamine pyrophosphate, Flavin adenine dinucleotide or the like.

The amount of co-enzymes in the pharmaceutical composition/formulation of the present invention ranges from 5% by wt. to 10% by wt. of the composition formulation. The amount of co-enzymes in the pharmaceutical composition/formulation of the present invention ranges from 50 mg to 200 mg per unit dose.

The pharmaceutical composition can be formulated in the form of tablets, capsules, granules, powder, sachets, suspension, solution, modified release formulations, topical formulations, etc. The formulations of the present invention comprise suitable excipients such as diluents, disintegrants, binders, solubilizing agent, lubricants, glidants, solvents etc.

In a preferred embodiment, the pharmaceutical composition/formulation according to the present invention can be formulated for oral administration. For oral administration, the solid pharmaceutical compositions can be in the form of, but not limited to, tablets, capsules, pills, hard capsules filled with liquids or solids, soft capsules, powders or granules, sachet, etc. The compositions may further comprise pharmaceutically acceptable excipients. The preferred excipients are selected from diluents, disintegrants, binders, solubilizing agent, lubricants, glidants, solvents etc. and combinations thereof.

The diluents are selected from microcrystalline cellulose, lactose (anhydrous/monohydrate/spray dried), starch, cellulose powder, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, compressible sugar, confectioner's sugar, corn starch, pregelatinized starch, dextrates, dextrin, dextrose, erythritol, ethylcellulose, fructose, fumaric acid, glyceryl palmitostearate, isomalt, kaolin, lactitol, magnesium carbonate, magnesium oxide, maltodextrin, maltose, mannitol, medium-chain triglycerides, polydextrose, polymethacrylates, simethicone, sodium alginate, sodium chloride, sorbitol, sterilizable maize, sucrose, sugar spheres, sulfobutylether β-cyclodextrin, talc, tragacanth, trehalose, xylitol or the like. The amount of diluent in the pharmaceutical composition of the present invention ranges from 1% by wt. to 30% by wt. of the composition.

The disintegrating agent is select from croscarmellose sodium, crospovidone, carboxymethyl cellulose (sodium/calcium), sodium starch glycolate, alginic acid, calcium alginate, cellulose, powdered, chitosan, colloidal silicon dioxide, corn starch, docusate sodium, glycine, guar gum, hydroxypropyl cellulose low-substituted, magnesium aluminium silicate, methylcellulose, microcrystalline cellulose, polacrilin potassium, povidone, sodium alginate, pregelatinized starch or the like. The amount of disintegrating agent in the pharmaceutical composition of the present invention ranges from 1% by wt. to 7% by wt. of the composition.

The binder is selected from hypromellose, starch, acacia, agar, alginic acid, calcium carbonate, calcium lactate, carbomers, carboxymethylcellulose sodium, carrageenan, cellulose acetate phthalate, ceratonia, chitosan, copovidone, corn starch, pregelatinized starch, cottonseed oil, dextrates, dextrin, dextrose, ethylcellulose, gelatin, glyceryl behenate, guar gum, hydrogenated vegetable oil type I, hydroxyethyl cellulose, hydroxyethylmethyl cellulose, hydroxypropyl cellulose, inulin, lactose, liquid glucose, low-substituted Hypromellose, magnesium aluminum silicate, maltodextrin, maltose, methylcellulose, microcrystalline cellulose, pectin, poloxamer, polycarbophil, polydextrose, polyethylene oxide, polymethacrylates, povidone, sodium alginate, stearic acid, sucrose, sunflower oil, tricaprylin, vitamin E polyethylene glycol succinate, zein or the like. The amount of binder in the pharmaceutical composition of the present invention ranges from 0.4% by wt. to 3% by wt. of the composition.

The solubilizing agent is selected from polysorbate 80, sodium lauryl sulfate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E polyethylene glycol succinate, microcrystalline cellulose, carboxymethylcellulose sodium, diethanolamine, ethylene glycol palmitostearate, glycerin monostearate, hypromellose, hypromellose acetate succinate, lecithin, polyethylene alkyl ethers, aluminum oxide, poly(methylvinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether β-cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like. The amount of Solubilizing Agent in the pharmaceutical composition of the present invention ranges from 0.5% by wt. to 3% by wt. of the composition.

The lubricant is selected from magnesium stearate, zinc stearate, calcium stearate, glycerin monostearate, glyceryl behenate, glyceryl palmitostearate, hydrogenated castor oil, hydrogenated vegetable oil type I, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium benzoate or the like. The amount of Lubricant in the pharmaceutical composition of the present invention ranges from 0.4% by wt. to 3% by wt. of the composition.

The glidant is selected from colloidal silicon dioxide, talc, calcium phosphate tribasic, cellulose powdered, hydrophobic colloidal silica, magnesium oxide, magnesium silicate, magnesium trisilicate, silicon dioxide or the like. The amount of Glidant in the pharmaceutical composition of the present invention ranges from 0.5% by wt. to 5 by wt, of the composition.

The solvent is selected from water, alcohol, isopropyl alcohol, propylene glycol, almond oil, benzyl alcohol, benzyl benzoate, butylene glycol, carbon dioxide, castor oil, corn oil (maize), cottonseed oil, dibutyl phthalate, diethyl phthalate, dimethyl ether, albumin, dimethyl phthalate, dimethyl sulfoxide, dimethylacetamide, ethyl acetate, ethyl lactate, ethyl oleate, glycerin, glycofurol, isopropyl myristate, isopropyl palmitate, light mineral oil, medium-chain triglycerides, methyl lactate, mineral oil, monoethanolamine, octyldodecanol, olive oil, peanut oil, polyethylene glycol, polyoxyl 35 castor oil, propylene carbonate, pyrrolidone, safflower oil, sesame oil, soybean oil, sunflower oil, triacetin, tricaprylin, triethanolamine, triethyl citrate, triolein, water-miscible solvents or the like. The amount of solvent in the pharmaceutical composition of the present invention is used in a quantity sufficient.

Developing pharmaceutical compositions or formulations wherein one or more ingredients are obtained from natural sources, like Natural FAAH Inhibitor/Natural Antioxidant, poses challenges for the formulator. Such challenges include providing a suitable size dosage form containing the effective amount of the active ingredients. Challenges also include providing stable formulations while retaining desirable pharmacokinetic properties. As currently understood, synthetic FAAH Inhibitors are not approved for therapeutic use in any country by any drug regulatory authority. The present invention provides stable and therapeutically effective compositions and formulations comprising PEA, one or more natural FAAH inhibitors and Cholecalciferol.

Some of the exemplary compositions of the present invention are described below:

Composition/Formulation 1

| S. No. | Ingredient | Amount (% w/w) |
|---|---|---|
| 1. | PEA | 30 to 70 |
| 2. | Natural FAAH Inhibitor(s) | 0.5 to 60 |
| 3. | Cholecalciferol | 0.05 to 10 |

Composition/Formulation 2

| S. No. | Ingredient | Amount (% w/w) |
|---|---|---|
| 1. | PEA | 30 to 70 |
| 2. | Natural FAAH Inhibitor(s) | 0.5 to 60 |
| 3. | Cholecalciferol | 0.05 to 10 |
| 4. | Natural Anti-oxidant | 0.04 to 50 |

Composition/Formulation 3

| S. No. | Ingredient | Amount (% w/w) |
|---|---|---|
| 1. | PEA | 30 to 70 |
| 2. | Natural FAAH Inhibitor(s) | 0.5 to 60 |
| 3. | Cholecalciferol | 0.05 to 10 |
| 4. | Natural Anti-oxidant | 0.04 to 50 |
| 5. | Vitamin | 0.01 to 10 |

Composition/Formulation 4

| S. No. | Ingredient | Amount (% w/w) |
|---|---|---|
| 1. | PEA | 30 to 70 |
| 2. | Natural FAAH Inhibitor(s) | 0.5 to 60 |
| 3. | Cholecalciferol | 0.05 to 10 |
| 4. | Natural Anti-oxidant | 0.04 to 50 |
| 5. | Co-enzyme | 5 to 10 |

Composition/Formulation 5

| S. No. | Ingredient | Amount (% w/w) |
|---|---|---|
| 1. | PEA | 30 to 70 |
| 2. | Natural FAAH Inhibitor(s) | 0.5 to 60 |
| 3. | Cholecalciferol | 0.05 to 10 |
| 4. | Natural Anti-oxidant | 0.04 to 50 |
| 5. | Vitamin | 0.01 to 10 |
| 6. | Co-enzyme | 5 to 10 |

General Process for Preparation of the Formulations of the Present Invention

1. Accurately weigh all material in separate containers.
2. Sift previously weighed active Ingredients (PEA, Natural FAAH Inhibitor(s) or natural anti-oxidant(s)), diluent(s) and disintegrating agent(s) separately through sieve #40.
3. Mix content of step 2 in rapid to granulator (RMG) with an impeller at slow speed.
4. Binder solution Preparation: In a separate container, take Purified water and dissolve a binding agent and solubilizing agent to obtain a clear, yellowish solution and Cholecalciferol to get the hazy solution.
5. Add a binder solution to step 3 in the RMG at slow speed.
6. Transfer the granulated wet mass obtained into a bowl and carry out drying in a Fluid bed dryer at air dry for 30 minutes. Then, sift semi dried granules through sieve #12. Perform size reduction of the granules retained on sieve #12 using a Multi-mill with 8.0 mm screen.
7. Transfer the obtained semi dried mass into a bowl and carry out drying in a Fluid bed dryer at 55° C.±5° C. until the level or dryness (LOD) of the blend is reduced to 1.3 to 1.7% w/w.
8. Sift semi dried granules through sieve #14. Perform size reduction of the granules retained on sieve #16 using a Multi-mill with 2.5 mm screen.
9. Sift the obtained dried granules through sieve #16. Perform size reduction of the granules retained on sieve #2 using a Multi-mill 1.5 mm screen.
10. Sift previously weighed disintegrant(s) and glidant(s) through sieve #40 and mix with Step-9 for 10 minutes.
11. Sift previously weighed lubricant(s) through sieve #40 and mix with Step-10 for 5 minutes
12. Compressing the granules obtained above into tablet.

EXAMPLES

It is understood that the foregoing examples are merely illustrative of the present invention. Certain modifications of the articles and/or methods employed may be made and still achieve the objectives of the invention. Such modifications are contemplated as within the scope of the claimed invention. For Experiments Natural FAAH inhibitors were obtained from Navpad Trade Impex, Office No. 215, Sai Chamber, Near Bus Depot, Santacruz (East), Mumbai—400055; Natural Anti-oxidants were from Genotek Biochem, Office: D-619 Neelkanth Business Park, Next to Vidyavihar Railway Station, Nathani Road, Vidyavihar (West), Mumbai—400086 and Cholecalciferol from Stabicoat Vitamins, 47, Sardar Panel Industrial Estate, Narol, Ahmedabad.

Example 1

| S. No | Ingredients | % w/w |
|---|---|---|
| | Intragranular Ingredients | |
| 1 | Micronized PEA | 46.15 |
| 2 | Quercetin | 15.38 |
| 3 | Resveratrol | 23.08 |
| 4 | MCC pH 101 | 3.18 |
| 5 | Croscarmellose sodium | 3.08 |
| | Binder Solution | |
| 6 | PVP K-30 | 1.08 |
| 7 | Polysorbate 80 | 1.54 |
| 8 | Cholecalciferol (400 IU = 0.8 mg) | 0.12 |
| 9 | Water | QS |
| | Extragranular Ingredients | |
| 10 | Croscarmellose sodium | 1.54 |
| 11 | Talc | 1.77 |
| 12 | Colloidal silicon dioxide | 3.08 |
| | Final Wt. of Tablet | 100.00 |

Example 2

| S. No | Ingredients | % w/w |
|---|---|---|
| | Intragranular Ingredients | |
| 1 | Micronized PEA | 41.38 |
| 2 | Quercetin | 34.48 |
| 3 | Resveratrol | 10.34 |
| 4 | Lactose monohydrate | 1.48 |
| 5 | Sodium starch glycolate | 1.38 |
| | Binder Solution | |
| 6 | PVP K-30 | 0.48 |
| 7 | Polysorbate 80 | 0.69 |
| 8 | Cholecalciferol (50000 IU) | 6.90 |
| 9 | Isopropyl Alcohol | QS |
| 10 | Water | QS |
| | Extragranular Ingredients | |
| 11 | Sodium starch glycolate | 0.69 |
| 12 | Magnesium Stearate | 0.79 |
| 13 | Colloidal silicon dioxide | 1.38 |
| | Final Wt. of Tablet | 100.00 |

Example 3

| S. No | Ingredients | % w/w |
|---|---|---|
| | Intragranular Ingredients | |
| 1 | Micronized PEA | 33.33 |
| 2 | Quercetin | 11.11 |
| 3 | Resveratrol | 33.33 |
| 4 | Dicalcium phosphate | 5.04 |
| 5 | Crospovidone | 4.44 |
| | Binder Solution | |
| 6 | HPMC 5 Cps | 1.11 |
| 7 | Sodium Lauryl sulphate | 2.22 |
| 8 | Cholecalciferol (400 IU) | 0.18 |
| 9 | Isopropyl Alcohol | QS |
| 10 | Dichloromethane | QS |
| | Extragranular Ingredients | |
| 12 | Crospovidone | 2.22 |
| 13 | Magnesium Stearate | 2.56 |
| 14 | Colloidal silicon dioxide | 4.44 |
| | Final Wt. of Tablet | 100.00 |

Example 4

| S. No | Ingredients | % w/w |
|---|---|---|
| | Intragranular Ingredients | |
| 1 | Micronized PEA | 60.00 |
| 2 | Cholecalciferol | 0.16 |
| 3 | Quercetin | 20.00 |
| 4 | Microcrystalline Cellulose pH 101 | 9.44 |
| 5 | Croscarmellose sodium | 3.00 |
| | Binder Solution | |
| 6 | PVP K 30 | 1.40 |
| 7 | Polysorbate 80 | 2.00 |
| 8 | Water | QS |
| | Extragranular Ingredients | |
| 9 | Croscarmellose sodium | 3.00 |
| 10 | Magnesium Stearate | 1.00 |
| | Final Wt. of Tablet | 100.00 |

Example 5

| S. No | Ingredients | % w/w |
|---|---|---|
| | Intragranular Ingredients | |
| 1 | Micronized PEA | 60.00 |
| 2 | Cholecalciferol | 0.16 |
| 3 | Myricetin | 20.00 |
| 4 | Lactose monohydrate | 9.44 |
| 5 | Sodium starch glycolate | 3.00 |
| | Binder Solution | |
| 6 | PVP K 30 | 1.40 |
| 7 | Sodium lauryl sulfate | 2.00 |
| 8 | Isopropyl Alcohol | QS |
| 9 | Dichloromethane | QS |
| | Extragranular Ingredients | |
| 10 | Sodium starch glycolate | 3.00 |
| 11 | Talc | 1.00 |
| | Final Wt. of Tablet | 100.00 |

Example 6

| S. No | Ingredients | % w/w |
|---|---|---|
| | Intragranular Ingredients | |
| 1 | Micronized PEA | 66.67 |
| 2 | Cholecalciferol | 0.18 |
| 3 | Isorhamnetin | 11.11 |

Example 7

| S. No | Ingredients | % w/w |
|---|---|---|
| | Intragranular Ingredients | |
| 1 | Micronized PEA | 60.00 |
| 2 | Cholecalciferol | 0.16 |
| 3 | Kaempferol | 20.00 |
| 4 | Mannitol | 9.44 |
| 5 | Crospovidone | 3.00 |
| | Binder Solution | |
| 6 | PVP K 30 | 1.40 |
| 7 | Sodium lauryl sulfate | 2.00 |
| 8 | Water | QS |
| | Extragranular Ingredients | |
| 9 | Crospovidone | 3.00 |
| 10 | Talc | 1.00 |
| | Final Wt. of Tablet | 100.00 |

-continued

| S. No | Ingredients | % w/w |
|---|---|---|
| 4 | Dicalcium Phosphate | 10.49 |
| 5 | Croscarmellose sodium | 3.33 |
| | Binder Solution | |
| 6 | HPMC 5 cps | 1.56 |
| 7 | Polysorbate 80 | 2.22 |
| 8 | Water | QS |
| | Extragranular Ingredients | |
| 9 | Croscarmellose sodium | 3.33 |
| 10 | Magnesium Stearate | 1.11 |
| | Final Wt. of Tablet | 100.00 |

Example 8

| S. No | Ingredients | % w/w |
|---|---|---|
| | Intragranular Ingredients | |
| 1 | Micronized PEA | 65.22 |
| 2 | Cholecalciferol | 0.17 |
| 3 | Pristimerin | 10.87 |
| 4 | Microcrystalline Cellulose pH 101 | 12.43 |
| 5 | Croscarmellose sodium | 3.26 |
| | Binder Solution | |
| 6 | PVP K 30 | 1.52 |
| 7 | Polysorbate 80 | 2.17 |
| 8 | Water | QS |
| | Extragranular Ingredients | |
| 9 | Croscarmellose sodium | 3.26 |
| 10 | Magnesium Stearate | 1.09 |
| | Final Wt. of Tablet | 100.00 |

Example 9

| S. No | Ingredients | % w/w |
|---|---|---|
| | Intragranular Ingredients | |
| 1 | Micronized PEA | 33.33 |
| 2 | Cholecalciferol | 0.09 |
| 3 | Quercetin | 55.56 |
| 4 | Lactose monohydrate | 5.24 |
| 5 | Sodium starch Glycolate | 1.67 |
| | Binder Solution | |
| 6 | HPMC 5 cps | 0.78 |
| 7 | Sodium lauryl sulfate | 1.11 |
| 8 | Isopropyl Alcohol | QS |
| 9 | Dichloromethane | QS |
| | Extragranular Ingredients | |
| 9 | Sodium starch Glycolate | 1.67 |
| 10 | Talc | 0.56 |
| | Final Wt. of Tablet | 100.00 |

Example 10

| S. No | Ingredients | % w/w |
|---|---|---|
| | Intragranular Ingredients | |
| 1 | Micronized PEA | 60.00 |
| 2 | Cholecalciferol | 0.16 |
| 3 | Biochanin | 5.20 |
| 4 | Dicalcium Phosphate | 24.24 |
| 5 | Crospovidone | 3.00 |
| | Binder Solution | |
| 6 | PVP K 30 | 1.40 |
| 7 | Polysorbate 80 | 2.00 |
| 8 | Water | QS |
| | Extragranular Ingredients | |
| 9 | Crospovidone | 3.00 |
| 10 | Magnesium Stearate | 1.00 |
| | Final Wt. of Tablet | 100.00 |

Example 11

| S. No | Ingredients | % w/w |
|---|---|---|
| | Intragranular Ingredients | |
| 1 | Micronized PEA | 60.00 |
| 2 | Cholecalciferol | 0.16 |
| 3 | Genistein | 20.00 |
| 4 | Mannitol | 9.44 |
| 5 | Croscarmellose sodium | 3.00 |
| | Binder Solution | |
| 6 | PVP K 30 | 1.40 |
| 7 | Polysorbate 80 | 2.00 |
| 8 | Water | QS |
| | Extragranular Ingredients | |
| 9 | Croscarmellose sodium | 3.00 |
| 10 | Talc | 1.00 |
| | Final Wt. of Tablet | 100.00 |

Example 12

| S. No | Ingredients | % w/w |
|---|---|---|
| | Intragranular Ingredients | |
| 1 | Micronized PEA | 60.00 |
| 2 | Cholecalciferol | 0.16 |
| 3 | Daidzein | 20.00 |
| 4 | Microcrystalline Cellulose pH 101 | 9.44 |
| 5 | Sodium starch glycolate | 3.00 |
| | Binder Solution | |
| 6 | HPMC 5 cps | 1.40 |
| 7 | Polysorbate 80 | 2.00 |
| 8 | Isopropyl Alcohol | QS |
| 9 | Dichloromethane | QS |
| | Extragranular Ingredients | |
| 10 | Sodium starch glycolate | 3.00 |
| 11 | Magnesium Stearate | 1.00 |
| | Final Wt. of Tablet | 100.00 |

Example 13

| S. No | Ingredients | % w/w |
|---|---|---|
| | Intragranular Ingredients | |
| 1 | Micronized PEA | 59.52 |
| 2 | Cholecalciferol | 0.16 |
| 3 | Genistein | 0.79 |
| 4 | Quercetin | 19.84 |
| 5 | Microcrystalline Cellulose pH 101 | 9.37 |
| 6 | Croscarmellose sodium | 2.98 |
| | Binder Solution | |
| 7 | PVP K 30 | 1.39 |
| 8 | Polysorbate 80 | 1.98 |
| 9 | Water | QS |
| | Extragranular Ingredients | |
| 10 | Croscarmellose sodium | 2.98 |
| 11 | Magnesium Stearate | 0.99 |
| | Final Wt. of Tablet | 100.00 |

Example 14

| S. No | Ingredients | % w/w |
|---|---|---|
| | Intragranular Ingredients | |
| 1 | Micronized PEA | 40.00 |
| 2 | Cholecalciferol | 0.11 |
| 3 | Quercetin | 13.33 |
| 4 | Resveratrol | 33.33 |
| 5 | Lactose monohydrate | 6.29 |
| 6 | Sodium starch glycolate | 2.00 |
| | Binder Solution | |
| 7 | HPMC 5 cps | 0.93 |
| 8 | Polysorbate 80 | 1.33 |
| 9 | Isopropyl Alcohol | QS |
| 10 | Dichloromethane | QS |

-continued

| S. No | Ingredients | % w/w |
|---|---|---|
| | Extragranular Ingredients | |
| 11 | Sodium starch glycolate | 2.00 |
| 12 | Talc | 0.67 |
| | Final Wt. of Tablet | 100.00 |

Example 15

| S. No | Ingredients | % w/w |
|---|---|---|
| | Intragranular Ingredients | |
| 1 | Micronized PEA | 60.00 |
| 2 | Cholecalciferol | 0.16 |
| 3 | Quercetin | 20.00 |
| 4 | Vitamin E | 6.00 |
| 5 | Dicalcium phosphate | 3.44 |
| 6 | Crospovidone | 3.00 |
| | Binder Solution | |
| 7 | PVP K 30 | 1.40 |
| 8 | Sudium Lauryl sulfate | 2.00 |
| 9 | Water | QS |
| | Extragranular Ingredients | |
| 10 | Crospovidone | 3.00 |
| 11 | Magnesium Stearate | 1.00 |
| | Final Wt. of Tablet | 100.00 |

Example 16

| S. No | Ingredients | % w/w |
|---|---|---|
| | Intragranular Ingredients | |
| 1 | Micronized PEA | 30.00 |
| 2 | Cholecalciferol | 0.08 |
| 3 | Quercetin | 10.00 |
| 4 | Glutathione | 50.00 |
| 5 | Mannitol | 4.72 |
| 6 | Croscarmellose sodium | 1.50 |
| | Binder Solution | |
| 7 | HPMC 5 cps | 0.70 |
| 8 | Polysorbate 80 | 1.00 |
| 9 | Isopropyl Alcohol | QS |
| 10 | Dichloromethane | QS |
| | Extragranular Ingredients | |
| 11 | Croscarmellose sodium | 1.50 |
| 12 | Talc | 0.50 |
| | Final Wt. of Tablet | 100.00 |

Example 17

| S. No | Ingredients | % w/w |
|---|---|---|
| | Intragranular Ingredients | |
| 1 | Micronized PEA | 60.00 |
| 2 | Cholecalciferol | 0.16 |
| 3 | Quercetin | 20.00 |
| 4 | Selenium | 0.04 |
| 5 | Microcrystalline Cellulose pH 101 | 9.40 |
| 6 | Sodium starch glycolate | 3.00 |
| | Binder Solution | |
| 6 | PVP K 30 | 1.40 |
| 7 | Polysorbate 80 | 2.00 |
| 8 | Water | QS |
| | Extragranular Ingredients | |
| 9 | Sodium starch glycolate | 3.00 |
| 10 | Magnesium Stearate | 1.00 |
| | Final Wt. of Tablet | 100.00 |

Example 18

| S. No | Ingredients | % w/w |
|---|---|---|
| | Intragranular Ingredients | |
| 1 | Micronized PEA | 57.14 |
| 2 | Cholecalciferol | 0.08 |
| 3 | Quercetin | 9.52 |
| 4 | Resveratrol | 23.81 |
| 5 | Lactose monohydrate | 4.50 |
| 6 | Crospovidone | 1.43 |
| | Binder Solution | |
| 7 | HPMC 5 cps | 0.67 |
| 8 | Polysorbate 80 | 0.95 |
| 9 | Water | QS |
| | Extragranular Ingredients | |
| 10 | Crospovidone | 1.43 |
| 11 | Magnesium Stearate | 0.48 |
| | Final Wt. of Tablet | 100.00 |

Example 19

| S. No | Ingredients | % w/w |
|---|---|---|
| | Intragranular Ingredients | |
| 1 | Micronized PEA | 40.00 |
| 2 | Cholecalciferol | 0.11 |
| 3 | Quercetin | 13.33 |
| 4 | Resveratrol | 33.33 |
| 5 | Dicalcium phosphate | 6.29 |
| 6 | Croscarmellose sodium | 2.00 |
| | Binder Solution | |
| 7 | PVP K 30 | 0.93 |
| 8 | Sodium lauryl sulfate | 1.33 |
| 9 | Isopropyl alcohol | QS |
| 10 | Purified Water | QS |

-continued

| S. No | Ingredients | % w/w |
|---|---|---|
| | Extragranular Ingredients | |
| 11 | Croscarmellose sodium | 2.00 |
| 12 | Talc | 0.67 |
| | Final Wt. of Tablet | 100.00 |

Example 20

| S. No | Ingredients | % w/w |
|---|---|---|
| | Intragranular Ingredients | |
| 1 | Micronized PEA | 57.14 |
| 2 | Cholecalciferol | 0.08 |
| 3 | Quercetin | 9.52 |
| 4 | Resveratrol | 23.81 |
| 5 | Mannitol | 4.50 |
| 6 | Sodium starch glycolate | 1.43 |
| | Binder Solution | |
| 7 | PVP K 30 | 0.67 |
| 8 | Polysorbate 80 | 0.95 |
| 9 | Purified Water | QS |
| | Extragranular Ingredients | |
| 10 | Sodium starch glycolate | 1.43 |
| 11 | Magnesium Stearate | 0.48 |
| | Final Wt. of Tablet | 100.00 |

Example 21

| Sr. No | Ingredients | % w/w |
|---|---|---|
| | Intragranular Ingredients | |
| 1 | Micronized PEA | 60.00 |
| 2 | Cholecalciferol | 0.16 |
| 3 | Quercetin | 20.00 |
| 4 | Microcrystalline Cellulose pH 101 | 9.42 |
| 5 | Croscarmellose sodium | 3.00 |
| | Binder Solution | |
| 6 | PVP K 30 | 1.40 |
| 7 | Methylcobalamin | 0.02 |
| 8 | Polysorbate 80 | 2.00 |
| 9 | Water | QS |
| | Extragranular Ingredients | |
| 10 | Croscarmellose sodium | 3.00 |
| 11 | Magnesium Stearate | 1.00 |
| | Final Wt. of Tablet | 100.00 |

Example 22

| S. No | Ingredients | % w/w |
|---|---|---|
| | Intragranular Ingredients | |
| 1 | Micronized PEA | 46.15 |
| 2 | Quercetin | 15.38 |

-continued

| S. No | Ingredients | % w/w |
|---|---|---|
| 3 | Resveratrol | 23.08 |
| 4 | Lactose Monohydrate | 2.57 |
| 5 | Sodium Starch Glycolate | 3.08 |
| | Binder Solution | |
| 6 | PVP K-30 | 1.08 |
| 7 | Polysorbate 80 | 1.54 |
| 8 | Cholecalciferol (400 IU = 0.8 mg) | 0.12 |
| 9 | Cyanocobalamin | 0.62 |
| 10 | Water | QS |
| | Extragranular Ingredients | |
| 11 | Sodium Starch Glycolate | 1.54 |
| 12 | Magnesium Stearate | 1.77 |
| 13 | Colloidal silicon dioxide | 3.08 |
| | Final Wt. of Tablet | 100.00 |

Example 23

| S. No | Ingredients | % w/w |
|---|---|---|
| | Intragranular Ingredients | |
| 1 | Micronized PEA | 54.55 |
| 2 | Cholecalciferol | 0.15 |
| 3 | Quercetin | 18.18 |
| 4 | Ubidecarenone | 9.09 |
| 5 | Mannitol | 8.58 |
| 6 | Crospovidone | 2.73 |
| | Binder Solution | |
| 7 | PVP K 30 | 1.27 |
| 8 | Polysorbate 80 | 1.82 |
| 9 | Water | QS |
| | Extragranular Ingredients | |
| 10 | Crospovidone | 2.73 |
| 11 | Magnesium Stearate | 0.91 |
| | Final Wt. of Tablet | 100.00 |

Example 24

| Sr. No | Ingredients | % w/w |
|---|---|---|
| | Intragranular Ingredients | |
| 1 | Micronized PEA | 42.86 |
| 2 | Quercetin | 14.29 |
| 3 | Resveratrol | 21.43 |
| 4 | Thiamine Pyrophosphate | 7.14 |
| 5 | Dicalcium stearate | 2.96 |
| 6 | Croscarmellose sodium | 2.86 |
| | Binder Solution | |
| 7 | HPMC 5 cps | 1.00 |
| 8 | Polysorbate 80 | 1.43 |
| 9 | Cholecalciferol (400 IU = 0.8 mg) | 0.11 |
| 10 | Water | QS |
| | Extragranular Ingredients | |
| 11 | Croscarmellose sodium | 1.43 |
| 12 | Magnesium stearate | 1.64 |
| 13 | Colloidal silicon dioxide | 2.86 |
| | Final Wt. of Tablet | 100.00 |

Example 25

| S. No | Ingredients | % w/w |
|---|---|---|
| | Intragranular Ingredients | |
| 1 | Micronized PEA | 42.86 |
| 2 | Quercetin | 14.29 |
| 3 | Resveratrol | 21.43 |
| 4 | Ubidecarenone | 7.14 |
| 5 | MCC pH 101 | 2.94 |
| 6 | Croscarmellose sodium | 2.86 |
| | Binder Solution | |
| 7 | PVP K-30 | 1.00 |
| 8 | Polysorbate 80 | 1.43 |
| 9 | Cholecalciferol (400 IU = 0.8 mg) | 0.11 |
| 10 | Methylcobalamin | 0.01 |
| 11 | Water | QS |
| | Extragranular Ingredients | |
| 12 | Croscarmellose sodium | 1.43 |
| 13 | Magnesium stearate | 1.64 |
| 14 | Colloidal silicon dioxide | 2.86 |
| | Final Wt. of Tablet | 100.00 |

Example 26

| S. No | Ingredients | % w/w |
|---|---|---|
| | Intragranular Ingredients | |
| 1 | Micronized PEA | 30.00 |
| 2 | Cholecalciferol | 5.00 |
| 3 | Quercetin | 25.00 |
| 4 | Glutathione | 12.50 |
| 5 | Benfotiamine | 10.00 |
| 6 | Ubidecarenone | 10.00 |
| 7 | Microcrystalline Cellulose pH 101 | 4.75 |
| 8 | Croscarmellose sodium | 1.00 |
| | Binder Solution | |
| 9 | PVP K 30 | 0.50 |
| 10 | Polysorbate 80 | 0.50 |
| 11 | Water | QS |
| | Extragranular Ingredients | |
| 12 | Colloidal silicone dioxide | 0.50 |
| 13 | Magnesium Stearate | 0.25 |
| | Final Wt. of Sachet | 100.00 |

Stability Study

Example 27

Stability Study of Formulation of Example 1

Stability Condition: Accelerated Stability Testing: 40° C., 75% RH

| | | | Duration of Study | | | |
|---|---|---|---|---|---|---|
| S. No. | TEST | Specification | Initial | 1 Months | 3 Months | 6 Months |
| 1.0 | Description | Yellow Colored, Capsule shaped uncoated tablets | Complies | Complies | Complies | Complies |
| 2.0 | Average weight of 20 tablets | 13.0 gm ± 5% | 13.1 gm | 13.2 gm | 12.9 gm | 13.2 gm |
| 3.0 | Average weight of tablet | 650 mg ± 5% | 655 mg | 660 mg | 645 mg | 660 mg |
| 4.0 | Friability | Not more than 1.0% | 0.25% | 0.25% | 0.25% | 0.25% |
| 5.0 | Hardness | Not less than 5.0 Kg/cm$^2$ | 8.5 Kg/cm$^2$ | 7.5 Kg/cm$^2$ | 7.0 Kg/cm$^2$ | 8.5 Kg/cm$^2$ |
| 6.0 | Disintegration Test | Not more than 15 minutes | 7-8 minutes | 8-9 minutes | 7-8 minutes | 8-9 minutes |
| 7.0 | | | Assay | | | |
| 7.1 | PEA | Between 90.0% to 110.0% | 106.2% | 107.3% | 100.4% | 108.2% |
| 7.2 | Quercetin | Between 90.0% to 110.0% | 98.9% | 100.4% | 98.4% | 99.0% |
| 7.3 | Resveratrol | Between 90.0% to 110.0% | 94.6% | 96.8% | 96.9% | 97.3% |
| 7.4 | Cholecalciferol | Not less than 90% (Label claim 400 IU) | 102.5% | 106.5% | 103.7% | 100.4% |
| 8.0 | | | Dissolution | | | |
| 8.1 | Dissolution of PEA | Not Less than 70% in 60 minutes | 89.8% | 87.3% | 86.7% | 88.4% |
| 8.2 | Dissolution of Quercetin | Not Less than 70% in 60 minutes | 86.1% | 86.8% | 87.3% | 86.9% |
| 8.3 | Dissolution of Resveratrol | Not Less than 70% in 60 minutes | 87.5% | 88.4% | 86.8% | 86.8% |
| 8.4 | Dissolution of Cholecalciferol | Not Less than 70% in 60 minutes | 91.2% | 90.9% | 91.2% | 91.3% |

Example 28

Stability Study of Formulation of Example 4

Stability Condition: Accelerated Stability Testing: 40° C., 75% RH

| | | | Duration of Study | | | |
|---|---|---|---|---|---|---|
| S. No. | TEST | Specification | Initial | 1 Months | 3 Months | 6 Months |
| 1.0 | Description | Yellow Colored, Capsule shaped uncoated tablets | Complies | Complies | Complies | Complies |
| 2.0 | Average weight of tablet | 500 mg ± 5% | 499.5 mg | 500.1 mg | 500.2 mg | 498.5 mg |
| 3.0 | Average weight of 20 tablets | 10.0 gm ± 5% | 10.1 gm | 10.0 gm | 10.2 gm | 9.9 gm |
| 4.0 | Friability | Not more than 1.0% | 0.28% | 0.31% | 0.35% | 0.29% |
| 5.0 | Hardness | Not less than 5.0 Kg/cm$^2$ | 7 Kg/cm$^2$ | 7.5 Kg/cm$^2$ | 7.0 Kg/cm$^2$ | 8.0 Kg/cm$^2$ |
| 6.0 | DisintegrationTest | Not more than 15 minutes | 5-6 minutes | 6-7 minutes | 5-6 minutes | 6-7 minutes |
| 7.0 | | | Assay | | | |
| 7.1 | PEA | Between 90.0% to 110.0% | 100.2% | 101.4% | 99.8% | 105.2% |
| 7.2 | Quercetin | Between 90.0% to 110.0% | 90.7% | 102.6% | 99.5% | 99.0% |

-continued

| S. No. | TEST | Specification | Duration of Study | | | |
|---|---|---|---|---|---|---|
| | | | Initial | 1 Months | 3 Months | 6 Months |
| 7.3 | Cholecalciferol | Not less than 90% (Label claim 400 IU) | 101.5% | 105.8% | 101.1% | 99.4% |
| 8.0 | | | Dissolution | | | |
| 8.1 | Dissolution of PEA | Not Less than 70% in 60 minutes | 88.9% | 91.5% | 90.1% | 89.4% |
| 8.2 | Dissolution of Quercetin | Not Less than 70% in 60 minutes | 94.2% | 90.1% | 89.9% | 86.1% |
| 8.3 | Dissolution of Cholecalciferol | Not Less than 70% in 60 minutes | 90.4% | 92.6% | 90.5% | 91.5% |

Example 29

Animal Study

Screening effect against 5/6 Nephrectomy induced chronic kidney disease (CKD) of synergistic combination or composition/formulation comprising PEA and other natural ingredients in rat. The following trials were carried out:

54 male Wistar rats (*Rat Rattus*) (6 per group) were maintained in animal house in a light/dark atmosphere based on a 12 hour cycle having temperature and relative humidity in the range of 25±2° C. and 30-70% respectively. To maintain the appropriate conditions, temperature and relative humidity were recorded three times daily. During complete experiment, animals were supplied with the standard certified rat pellet feed (manufactured by Keval sales corporation, Vadodara) and drinking water treated by the reverse osmosis ad libitum.

In order to evaluate the activity against chronic kidney disease, fifty four (54) male rats were screened and divided in to nine groups. For a comparative analysis, groups were divided as sham control (Group 1), disease control (Group 2), treatment groups with individual components (Group 3, Group 4, Group 5 and Group 6 as PEA, Cholecalciferol, Quercetin and Resveratrol respectively), test composition formulation of the present invention (Group 7 and Group 8 as PEA combinations) and reference standard drug (Group 9). Table 1 provides the details of the various groups and treatments conducted in the trial.

TABLE 1

| S. No. | Group | No. of Animals | Treatment (Dose) |
|---|---|---|---|
| 1 | G1 (Sham Control) | 6 | Sham Control |
| 2 | G2 (Disease Control) | 6 | Disease Control |
| 3 | G3 (PEA) | 6 | PEA (60 mg/kg, p.o.) |
| 4 | G4 (Cholecalciferol) | 6 | Cholecalciferol (0.17 mg/kg, p.o.) |
| 5 | G5 (Quercetin) | 6 | Quercetin (20 mg/kg, p.o.) |
| 6 | G6 (Resveratrol) | 6 | Resveratrol (30 mg/kg, p.o.) |
| 7 | G7 [Test Composition (PEA + Cholecalciferol + Quercetin)] | 6 | PEA (60 mg/kg, p.o.) + Cholecalciferol (0.17 mg/kg, p.o.) + Quercetin (20 mg/kg, p.o.) (Example 4) |

TABLE 1-continued

| S. No. | Group | No. of Animals | Treatment (Dose) |
|---|---|---|---|
| 8 | G8 [Test Composition (PEA + Cholecalciferol + Quercetin + Resveratrol)] | 6 | PEA (60 mg/kg, p.o.) + Cholecalciferol (0.17 mg/kg, p.o.) + Quercetin (20 mg/kg, p.o.) + Resveratrol (30 mg/kg, p.o.) (Example 1) |
| 9 | G9 (Reference drug) | 6 | Reference standard (20 mg/kg, p.o.) |

Treatment Protocol:

The animals under consideration were examined for a study period of 10 weeks and two-stage surgical procedure for kidney ligation and removal were performed.

Stage one: A ventral midline incision into the abdomen was made to expose the animal's left kidney, and the organ was freed from the surrounding tissue. A piece of suture was placed and ligated around each pole of the kidney at its one-third position. The one-third kidney on each pole was excised beyond the ligatures and the abdominal incision was closed.

Stage two: This procedure was performed 5-7 days after stage one. The animals were placed in ventral recumbancy and an incision was made parallel to the midline. The abdominal cavity was entered and the right kidney was made free from the surrounding tissue. The kidney was gently pulled out from the incision, and the adrenal gland was freed and replaced into the abdominal cavity. The renal blood vessels and the ureter were ligated or cauterized. The kidney was then removed by transecting the vessels and ureter just distal to the ligature or cauterized section. The skin incision was closed with wound clips.

Treatment. All treatment groups were treated on daily basis for 10 weeks after stage two of surgery. After completion of the study at the end of $10^{th}$ week, each group was analyzed in terms of the evaluating parameters such as blood collection, biochemistry analysis, urine analysis and histopathology of kidney.

Table 2 represents the summary of the results obtained by effect of administering of 'Test Composition/formulation' against 5/6 Nephrectomy induced Chronic Kidney Disease in rat

TABLE 2

| Group | Serum Analysis | | | | | | Urine Analysis Glomerular Filtration Rate | |
|---|---|---|---|---|---|---|---|---|
| | Creatinine | | BUN | | IL-6 | | | |
| | mg/dl | % Decreased Creatinine | mg/dl | % Decreased in BUN | pg/ml | % Decreased in IL-6 | ml/min/kg | % Increased GFR |
| G1 (Sham Control) | 0.83 | — | 30.46 | — | 129.67 | — | 8.00 | — |
| G2 (Disease Control) | 1.50 | — | 82.26 | — | 180.65 | — | 5.50 | — |
| G3 (PEA) | 1.12 | 25.63 | 60.98 | 25.87 | 162.18 | 10.22 | 6.50 | 18.18 |
| G4 (Cholecalciferol) | 1.40 | 7.02 | 75.63 | 8.05 | 178.45 | 1.22 | 5.65 | 2.73 |
| G5 (Quercetin) | 1.44 | 4.02 | 76.62 | 6.85 | 175.15 | 3.04 | 5.64 | 2.55 |
| G6 (Resveratrol) | 1.41 | 6.30 | 74.51 | 9.42 | 174.42 | 3.45 | 5.75 | 4.55 |
| G7 (P + Q + C) | 0.88 | 41.72 | 36.04 | 56.19 | 130.31 | 27.87 | 7.35 | 33.64 |
| G8 (P + Q + C + R) | 0.89 | 40.93 | 35.98 | 56.26 | 130.11 | 27.98 | 7.41 | 34.73 |
| G9 (Losartan) | 1.22 | 18.98 | 52.81 | 35.80 | 141.67 | 21.58 | 6.80 | 23.64 |

All above values are in mean

Interpretation and Inference

As there are many reasons behind the kidney diseases as discussed above in the specification, there are important biomarkers such as Serum Creatinine, Blood urea nitrogen (BUN) and IL-6 level to diagnose CKD wherein level of these parameters increases significantly.

This effect has been observed in rat model used in the study for 10 weeks wherein after induction of CKD, significant increase in the level or Serum Creatinine, BUN and IL-6 were observed when the activity of G2 compared with G1. This eventually confirms that the disease model was successfully induced with condition of CKD in all the animals.

Analysis of Important Biomarkers

As evident from the data summarized in the table 2, a significant reduction in serum creatinine and BUN and IL-6 have been observed in all animal groups.

The % decrease in creatinine by individual effect of the drug administered in groups G3, G4, G5, G6 and G9 were observed as 25.63, 7.02, 4.02, 6.30 and 18.98 respectively whereas the test composition(s) G7 and G8 of the present invention showed significant decrease by 41.72 and 40.93 respectively.

The % decrease in BUN by individual effect of the drug administered in groups G3, G4, G5, G6 and G9 were observed as 25.87, 8.05, 6.85, 9.42 and 35.80 respectively whereas the test composition(s) G7 and G8 of the present invention showed significant decrease by 56.19 and 56.26 respectively.

The % decrease in IL-6 by individual effect of the drug administered in groups G3, G4, G5, G6 and G9 were observed as 10.22, 1.22, 3.04, 3.45 and 21.58 respectively whereas the test composition(s) G7 and G8 of the present invention showed significant decrease by 27.87 and 27.98 respectively.

Similarly, in case of CKD patients, other important parameter for evaluation is glomerular filtration rate (GFR) which is reduced due to malfunction of the kidney. As evidenced in table 2, significant increase in GFR has been observed in all treatment groups.

The % increase in GFR by individual effect of the drug administered in groups G3, G4, G5, G6 and G9 were observed as 18.18, 2.73, 2.55, 4.55 and 23.64 respectively whereas the test composition(s) G7 and G8 of the present invention showed significant increase by 33.64 and 34.73 respectively.

Based on the above obtained result, it can be concluded that the test composition/formulation have synergistic activity over the individual components and also the treatment were effective to control the kidney functions.

Necroscopy Results

The color of kidney becomes fainted towards white in color in case of CKD in patients due to necrosis of kidney cells (nephron) and thereby poor blood supply and poor filtration through kidney. While examining during necropsy study, it was observed that in case of G2, the color of kidney was white due to severe kidney damage and thereby reduction of functioning of the kidney. Whereas in case of all treatment groups (G3-G9), the color of the kidney was brownish red due to improvement of the kidney function due to respective treatments.

Further, in case of CKD patient, in histopathology study, severe damage to nephron was evident. In the present experiment, there was significant disruption of nephrons observed in case of histopathology of kidney in G2 however, the damage to nephron was comparatively very less in all the treatment groups (G3-G9), particularly wherein the test composition/formulation were given.

Moreover, there was no mortality observed in case of any of the group of animals.

Conclusion

Based on the experimental study conducted on animals, it can be concluded that the test composition/formulation of the present invention was found to be more effective for improving or preventing progression of CKD caused by inflammation and/or Klotho under expression, and has a synergistic effect when compared with the individual drug.

Further, the necroscopy results also reveal that the pharmaceutical composition/formulation of the present invention was safe and effective for CKD patients.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the res tills arc contemplated in accordance with the objects and practices of the present invention. It is intended, therefore, that the invention be defined by the scope of the claims which follow and that such claims be interpreted as broadly as is reasonable.

We claim:

1. A pharmaceutical composition comprising a combination of:
   (a) 30 to 65% by wt. Palmitoylethanolamide (PEA);
   (b) One or more naturally occurring Fatty Acid Amine Hydrolase (FAAH) Inhibitors; and
   (c) 0.11 to 10% by wt. Cholecalciferol.

2. The pharmaceutical composition as claimed in claim 1, wherein the PEA is in micronized or non-micronized form.

3. The pharmaceutical composition as claimed in claim 1, wherein the naturally occurring FAAH Inhibitor is selected from Quercetin, Myricetin, Isorhamnetin, Kaempferol, Pristimerin, Biochanin A, Genistein, Daidzein or a combination thereof.

4. The pharmaceutical composition as claimed in claim 3, wherein the naturally occurring FAAH Inhibitor is selected from Quercetin, Genistein, Daidzein or a combination thereof.

5. The pharmaceutical composition as claimed in claim 1, wherein an amount of the naturally occurring FAAH inhibitor ranges from 0.5 to 60% by wt. of the composition.

6. The pharmaceutical composition as claimed in claim 1, wherein the composition further comprises a natural antioxidant, a vitamin, a coenzyme or a combination thereof.

7. The pharmaceutical composition as claimed in claim 6, wherein the natural antioxidant is selected from Resveratrol, Vitamin E, glutathione, selenium or a combination thereof.

8. The pharmaceutical composition as claimed in claim 6, wherein an amount of the natural antioxidant ranges from 0.04 to 50% by wt. of the composition.

9. The pharmaceutical composition as claimed in claim 6, wherein the vitamin is selected from methylcobalamin, cyanocobalamin, benfotiamine or a combination thereof.

10. The pharmaceutical composition as claimed in claim 6, wherein an amount of the vitamin ranges from 0.01 to 10% by wt. of the composition.

11. The pharmaceutical composition as claimed in claim 6, wherein the co-enzyme is selected from ubidecarenone, thiamine pyrophosphate, Flavin adenine dinucleotide or a combination thereof.

12. The pharmaceutical composition as claimed in claim 6, wherein an amount of the co-enzyme ranges from 5 to 10% by wt. of the composition.

13. The pharmaceutical composition as claimed in claim 1, further comprising pharmaceutically acceptable excipients.

14. The pharmaceutical composition as claimed in claim 13, wherein the pharmaceutically acceptable excipients are selected from a diluent, a disintegrant, a binder, a lubricant, a glidant, a solubilizing agent, a solvent, and combinations thereof.

15. The pharmaceutical composition as claimed in claim 14, wherein an amount of
    the diluent ranges from 1% to 30% by wt. of the composition,
    the disintegrant ranges from 1% to 7% by wt. of the composition,
    the binder ranges from 0.4% to 3% by wt. of the composition,
    the solubilizing agent ranges from 0.5% to 3% by wt. of the composition,
    the lubricant ranges from 0.4% to 3% by wt. of the composition,
    the glidant ranges from 0.5% to 5% by wt. of the composition, or
    the solvent is quantity sufficient.

16. The pharmaceutical composition as claimed in claim 1, wherein the composition is in the form of a tablet, capsule, pill, hard capsule filled with liquid or solid, soft capsule, sachet, powder, granule, suspension, solution or modified release formulation.

17. The pharmaceutical composition as claimed in claim 1, wherein the Cholecalciferol is 0.12 to 10% by wt.

* * * * *